US008920403B2

(12) United States Patent
Doerr

(10) Patent No.: US 8,920,403 B2
(45) Date of Patent: Dec. 30, 2014

(54) CATHETER WITH BIOLOGIC ADHESIVE INJECTION PORTS AND METHOD OF INJECTING BIOLOGIC ADHESIVE THEREWITH

(76) Inventor: Anthony Doerr, Missoula, MO (US)

(*) Notice: Subject to any disclaimer, the term of this patent is extended or adjusted under 35 U.S.C. 154(b) by 1051 days.

(21) Appl. No.: 12/406,218

(22) Filed: Mar. 18, 2009

(65) Prior Publication Data

US 2009/0240234 A1 Sep. 24, 2009

Related U.S. Application Data

(60) Provisional application No. 61/037,546, filed on Mar. 18, 2008.

(51) Int. Cl.
*A61M 25/00* (2006.01)
*A61M 25/10* (2013.01)

(52) U.S. Cl.
CPC ....... *A61M 25/0017* (2013.01); *A61M 25/0029* (2013.01); *A61M 25/0067* (2013.01); *A61M 25/0075* (2013.01); *A61M 25/10* (2013.01); *A61M 25/0068* (2013.01); *A61M 25/007* (2013.01); *A61M 2025/004* (2013.01); *A61M 2025/1093* (2013.01)
USPC .................. 604/523; 604/102.01; 604/96.01; 604/103.01; 604/544

(58) Field of Classification Search
CPC ............ A61M 25/10; A61M 25/1018; A61M 25/0125
USPC ............. 604/102.01, 96.01, 103.01, 523, 544
See application file for complete search history.

(56) References Cited

U.S. PATENT DOCUMENTS

| | | | |
|---|---|---|---|
| 2,854,982 A * | 10/1958 | Pagano | .................... 604/101.03 |
| 3,394,705 A | 7/1968 | Abramson | |
| 3,492,992 A * | 2/1970 | Kurtz | ............................ 604/272 |
| 3,595,713 A | 7/1971 | Bogoff | |
| 3,807,408 A | 4/1974 | Summers | |
| 3,977,408 A | 8/1976 | MacKew | |
| 4,211,233 A | 7/1980 | Lin | |
| 4,813,935 A | 3/1989 | Haber et al. | |
| 5,007,897 A * | 4/1991 | Kalb et al. | ....................... 604/43 |
| 5,213,580 A | 5/1993 | Slepian et al. | |
| 5,419,763 A | 5/1995 | Hildebrand | |
| 5,575,815 A | 11/1996 | Slepian et al. | |
| 5,855,563 A * | 1/1999 | Kaplan et al. | ................. 604/509 |
| 6,090,069 A | 7/2000 | Walker | |
| 6,139,520 A | 10/2000 | McCrory et al. | |

(Continued)

*Primary Examiner* — Kevin C Sirmons
*Assistant Examiner* — Edelmira Bosques
(74) *Attorney, Agent, or Firm* — John D. Wright; Dickinson Wright PLLC

(57) ABSTRACT

A catheter and method for draining a bladder and injecting a two part biologic adhesive is provided. The catheter has a tubular body extending between proximal and distal ends. A balloon is located adjacent the distal end with a first port extending between the proximal end and the balloon providing for inflation an deflation of the balloon. A second port extends substantially between the proximal end and the distal end for drainage. A pair of ports separate from one another and from the first and second ports extend between the proximal end and the balloon. The pair of ports are each arranged in fluid communication with separate openings located between the balloon and the proximal end to provide separate fluid flow paths for the separate components of the two part biologic adhesive between the proximal end and the openings.

5 Claims, 5 Drawing Sheets

(56) References Cited

U.S. PATENT DOCUMENTS

| | | |
|---|---|---|
| 6,296,632 B1 | 10/2001 | Luscher et al. |
| 6,508,777 B1 * | 1/2003 | Macoviak et al. ........... 604/4.01 |
| 6,629,947 B1 | 10/2003 | Sahatjian et al. |
| 6,939,381 B2 | 9/2005 | Stark et al. |
| 7,399,290 B2 | 7/2008 | Maki et al. |
| 2007/0249543 A1 | 10/2007 | Zadini et al. |
| 2008/0097297 A1 | 4/2008 | Kelley et al. |
| 2008/0114286 A1 | 5/2008 | Hamel et al. |

* cited by examiner

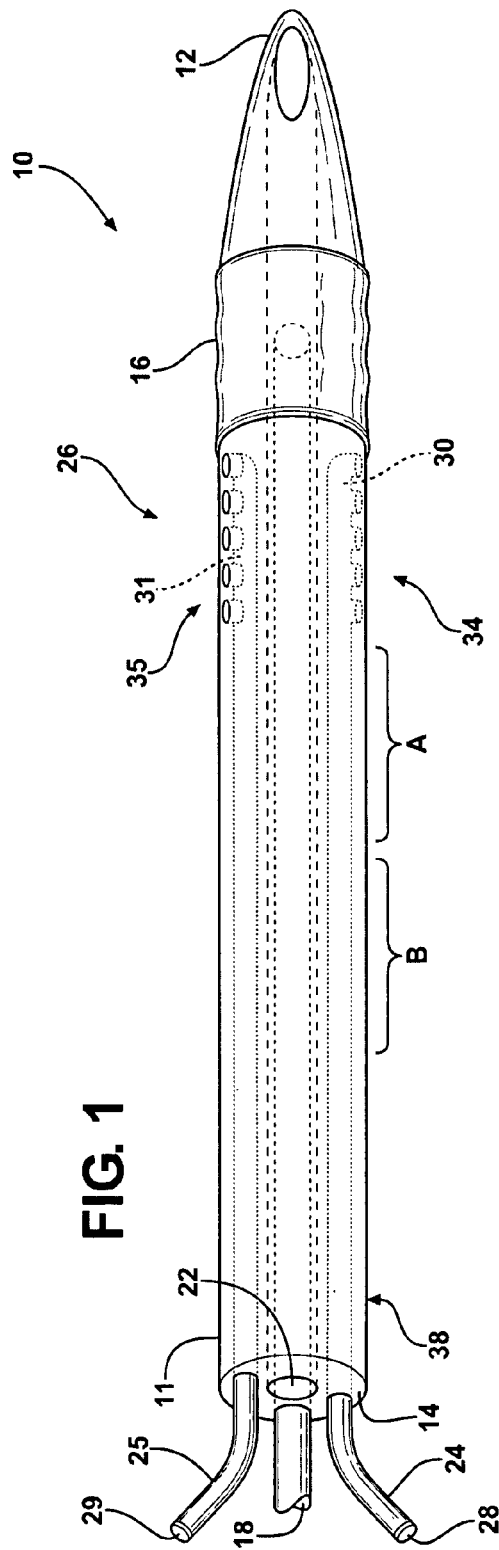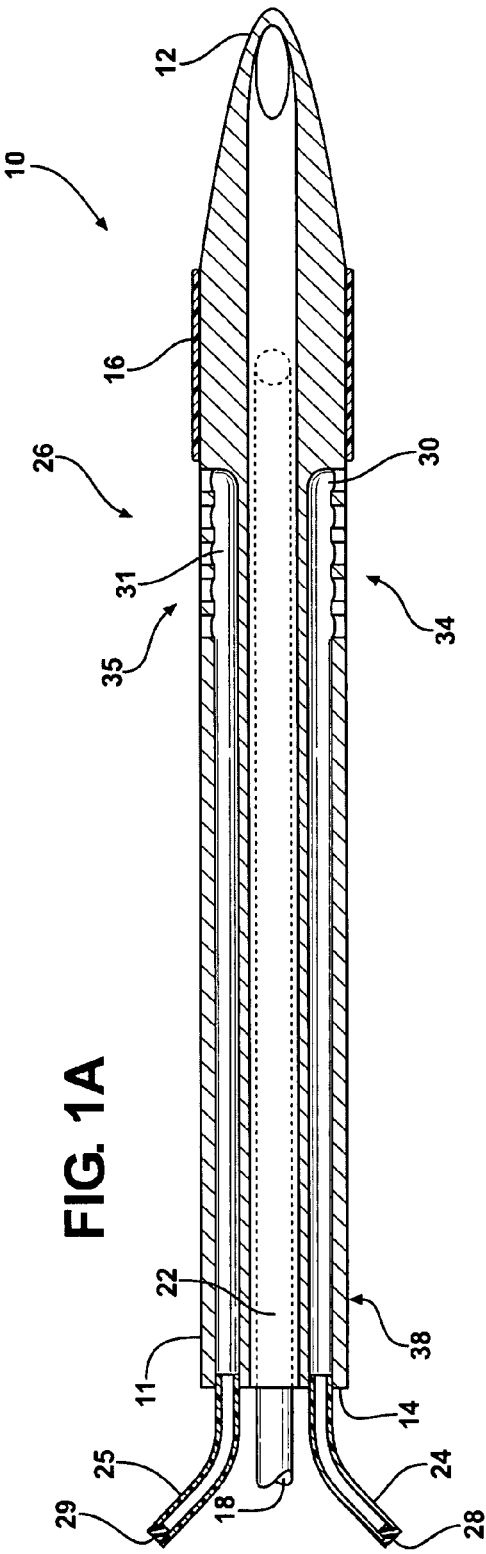
FIG. 1
FIG. 1A

US 8,920,403 B2

CATHETER WITH BIOLOGIC ADHESIVE INJECTION PORTS AND METHOD OF INJECTING BIOLOGIC ADHESIVE THEREWITH

CROSS-REFERENCE TO RELATED APPLICATION

This application claims the benefit of U.S. Provisional Application Ser. No. 61/037,546, filed Mar. 18, 2008, which is incorporated herein by reference in its entirety.

BACKGROUND OF THE INVENTION

1. Technical Field

This invention relates generally to apparatus and methods facilitating injection of a biologic adhesive, and more particularly to catheters having drainage and biologic adhesive injection ports.

2. Related Art

Frequently urologist have to deal with urinary tract bleeding. Urinary tract bleeding is typically prostate in origin as a result of benign prostate enlargement. The enlarged prostate can lead to increased vasculature to the prostate or large varicose veins that become prone to bleeding. The bleeding can result in urinary retention or inability to urinate due to the formation of clots. The bleeding symptoms can also occur in patients with prostate cancer, or following prostate surgeries, such as transurethral resection of the prostate (TURP) or laser prostatectomy.

Typically, in order to stop the aforementioned bleeding, a foley catheter having three ports is used. One of the ports is operable to inflate a balloon at a distal end of the catheter; another port provides an inflow path for irrigation and the other port provides an outflow path for the irrigant and urine. The catheter is inserted in the urethra to the desired position with the balloon located within the urethra. The balloon is inflated to both keep the catheter in place and to help tamponade or place pressure on the prostate to help stop the bleeding. The inflow port is used to introduce saline irrigation fluid into the urethra through the catheter to prevent the catheter from being plugged by clots, while the outflow port allows the irrigant and urine to flow outwardly of the urethra. This process is typically tedious, laborious (to ensure the catheter remains unplugged), and can take several days before the bleeding subsides.

SUMMARY OF THE INVENTION

According to one aspect of the invention, a catheter is provided. The catheter has a tubular body extending between proximal and distal ends and a balloon adjacent the distal end. A first port extends between the proximal end and the balloon in fluid communication with the balloon to provide a mechanism for inflation and deflation of the balloon. A second port extends between the proximal and distal ends across opposite sides of the balloon. The second port remains out of fluid communication with the first port. The tubular body further includes a pair of ports separate from the first and second ports and out of fluid communication with the first and second ports. Each of the pair of ports remain separate from one another and out of fluid communication with one another within the tubular body. The pair of ports exit separate openings outwardly from the tubular body between the proximal end and the balloon to provide separate fluid flow paths through the tubular body for separate components of a two part biologic adhesive.

According to another aspect of the invention, a method of injecting a two part biologic adhesive transurethrally is provided. The method includes inserting a catheter into a urethra; injecting separate parts of the biologic adhesive through separate ports in the catheter and radially outwardly through separate openings, and mixing the separate parts of the biologic adhesive in the urethra externally from the catheter.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

FIG. 1 is a side view of a catheter having a biologic adhesive system constructed in accordance with one presently preferred embodiment of the invention;

FIG. 1A is a cross-sectional view of the catheter of FIG. 1 taken generally through the biologic adhesive system;

DETAILED DESCRIPTION OF PRESENTLY PREFERRED EMBODIMENTS

Figure 2:
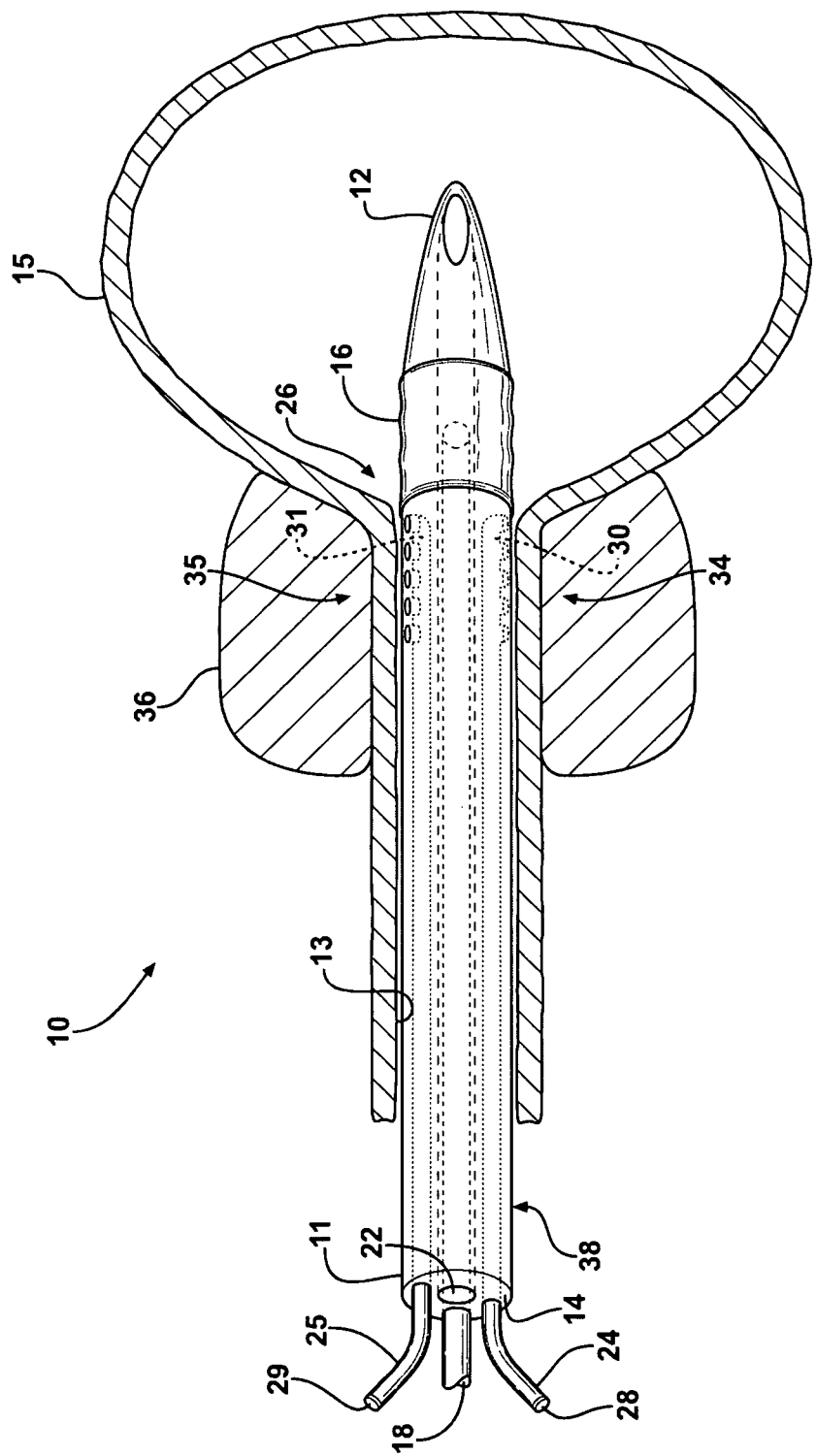
FIG. 2 is a side view of the catheter inserted into a urethra and into a bladder.
Figure 3:
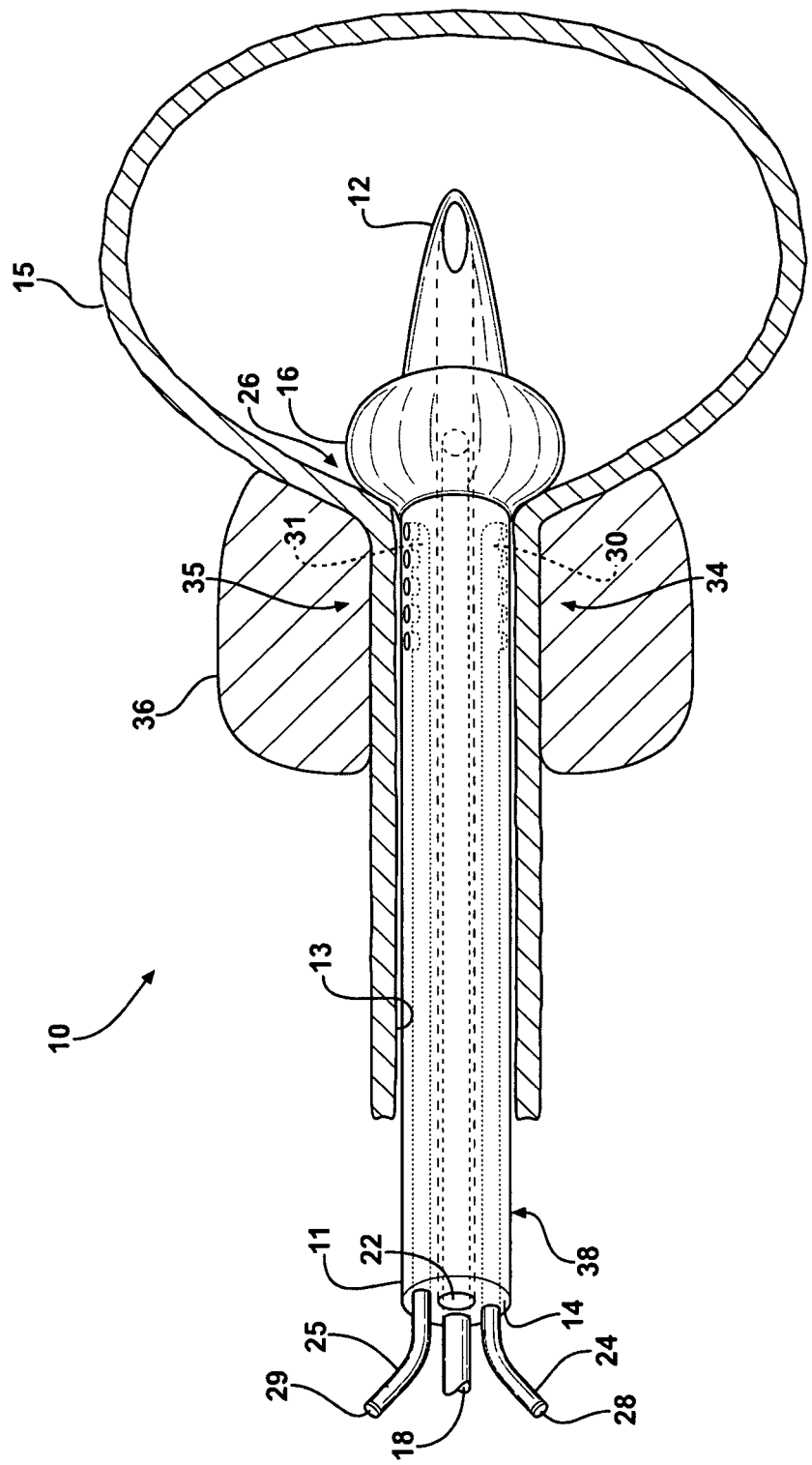
FIG. 3 is a view similar to FIG. 2 showing a balloon of the catheter inflated within the bladder.
Figure 4:
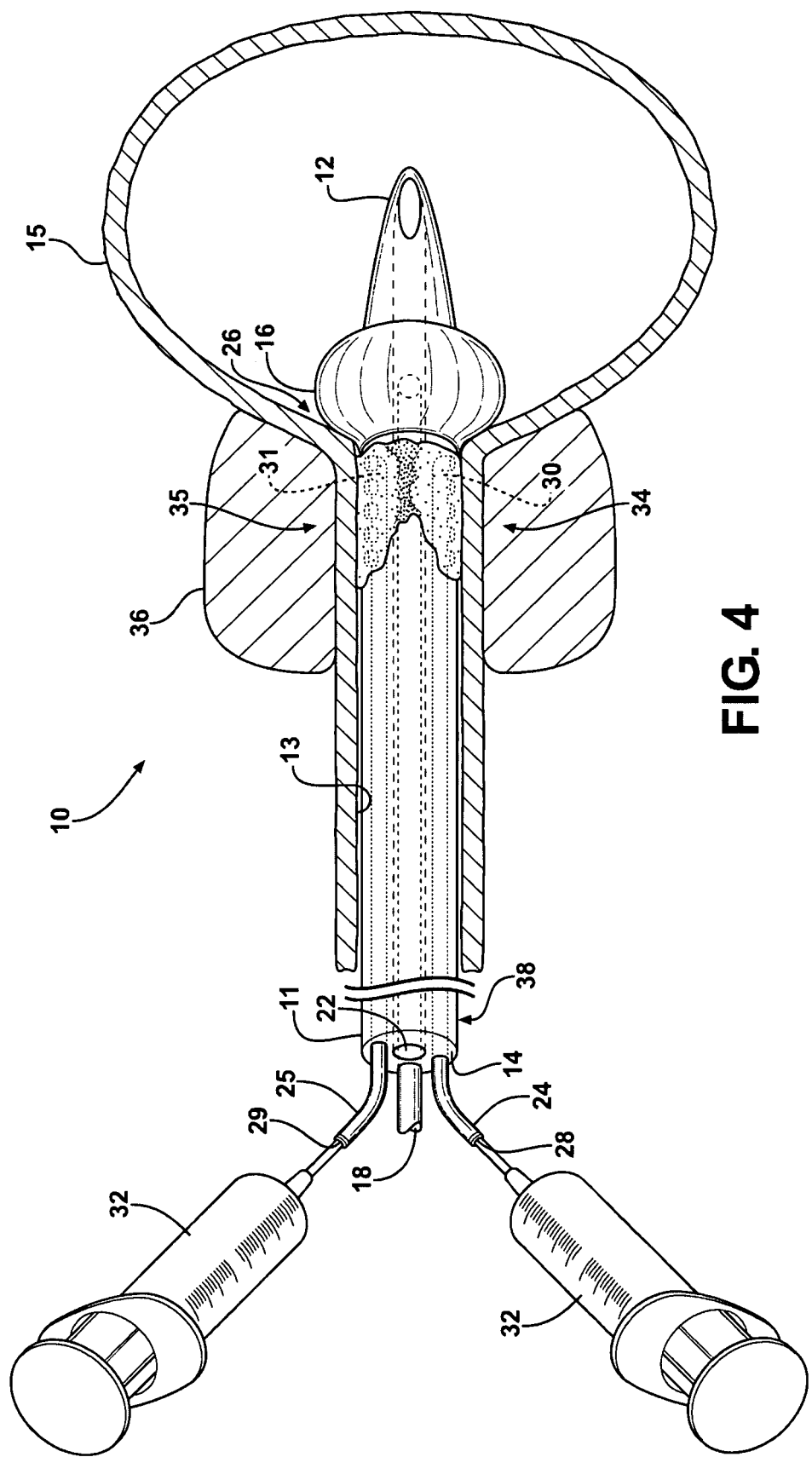
FIG. 4 is a view similar to FIG. 3 showing a biologic adhesive being injected into ports of the biologic adhesive system and out a plurality of openings.

Referring in more detail to the drawings, FIGS. 1-4 illustrate a catheter 10 constructed according to one presently preferred embodiment of the invention. The catheter 10 has a tubular body 11 extending from a distal end 12 to a proximal end 14. The distal end 12 is configured for insertion through a urethra 13 and into a bladder 15. An inflatable annular balloon 16 is located adjacent the distal end 12 with an associated first port, also referred to as an inflation port 18, extending from adjacent the proximal end 14 and being configured in communication with a lumen of the balloon 16 to provide a mechanism allowing inflation and deflation of the balloon 16. The catheter 10 also has a second port, referred to as a fluid drainage port 22, extending between the distal end 12 and the proximal end 14 and across opposite sides of the balloon 16 (the port 22 passes centrally through the balloon). As such, the drainage port 22 passes generally concentrically underneath the balloon 16 along a central longitudinal axis of the tubular body 11 to function as a fluid drainage passage to drain fluid from the bladder 15. In addition, the catheter 10 has as a pair of bioadhesive ports 24, 25 (corresponding to third and fourth ports, respectively), providing a portion of a bioadhesive injection system illustrated generally at 26 that allows a two part bioadhesive to be injected to a predetermined location within the urethra 13 while the catheter 10 is maintained in its intended location, such as by the balloon 16 while in an inflated state (FIGS. 3 and 4). Accordingly, the catheter 10 is configured to not only allow drainage of the bladder 15 through the drainage port 22, but also to allow the two part bioadhesive to be injected in its separate constituent parts to a precise location within the urethra to stop bleeding without allowing the two part adhesive to inadvertently react and clog the respective bioadhesive ports 24, 25.

The bioadhesive ports 24, 25 are shown here, by way of example and without limitation, as extending along diametrically opposite sides of the body 11 between respective proximal ends 28, 29 generally adjacent the proximal end 14 of the body 11 and respective distal ends shown generally at 30, 31. The ports 24, 25 can be integrally formed as a single piece of material with the catheter body 11, or otherwise formed from a separate piece of suitable tubing material and subsequently attached or molded to the catheter body 11. If the ports 24, 25 are attached to the body 11, it is preferable that they protrude outwardly a minimal distance from an outer surface 38 of the body, and more preferable that they remain flush or substantially flush with the outer surface 38 of the body 11. The ports 24, 25 remain out of fluid communication with one another internally to the catheter 10, and thus, there is no opportunity for the separate biologic adhesive components to become intermixed within the catheter 10.

The proximal ends 28, 29 of the bioadhesive ports 24, 25 can be configured to receive any suitable injector nozzle, such as on a syringe 32 (FIG. 4), in a generally fluid tight fit to facilitate injecting the bioadhesive from the injector nozzle of the syringe 32 into the bioadhesive ports 24, 25. The distal ends 30, 31 of the respective ports 24, 25 terminate at an opening or plurality of fenestrations or openings 34, 35 extending radially outwardly from the body 11. As such, the separate constituent ingredients of the two part bioadhesive are assured of remaining unmixed and separate from one another while traversing the full length of the separate bioadhesive ports 24, 25. It is only when the separate ingredients of the bioadhesive become expelled radially outwardly from the catheter 10 through the respective openings 34, 35 that the separate ingredients become mixed externally from the catheter 10. Accordingly, the ports 24, 25 are assured of remaining unclogged and free of mixed, coagulated or hardened bioadhesive material. The respective openings 34, 35 of each adhesive port 24, 25 are represented here as being arranged diametrically opposite one another, approximately 180 degrees from one another, thereby further guarding against inadvertent mixing of the separate bioadhesive constituent ingredients. Further, as illustrated, by way of example and without limitation, the openings 34, 35 can be located adjacent the balloon 16 on the proximal side of the balloon 16 (prostate urethral catheter). Accordingly, the openings 34, 35 are located between the balloon 16 and the proximal end 14 of the body 11. The openings 34, 35 can be provided of any suitable size and in any number and can extend along any desired length axially along the length of the catheter body 11 as best needed to apply the biologic adhesive over the presumed location of the bleeding and to accommodate the size of the source of bleeding. Accordingly, it should be recognized that the openings 34, 35, rather than being located immediately adjacent the balloon 16, could be located anywhere along the length of the catheter body 11, such as in the locations identified generally by A (penile urethral catheter) and B (bulbar urethral catheter) in FIG. 1.

In use, the catheter 10 is inserted into the urethra 13 to position the balloon 16 in the desired location prior to inflating the balloon (FIG. 2). Then, the balloon 16 is inflated via the inflation port 18 to maintain the catheter 10 in its intended position, shown here with the balloon 16 being inflated within the bladder 15 and positioned against a neck of the bladder and drawn against the prostate 36. With the balloon 16 inflated, the openings 34, 35 are located in the area of the bleeding. Then, a the biologic adhesive, such as Tisseal®, for example, which is a two part adhesive, is injected in its separate parts through the pair of adhesive ports 24, 25. The separate parts of the two part adhesive flow in an unmixed state through the separate ports 24, 25 and are expelled separately through the respective openings 34, 35. Upon flowing radially outwardly from the openings 34, 35, the two parts of the biologic adhesive admix externally to the catheter body 11 to form a glue-like clot or covering to the prostatic urethra around the catheter 10 to stop the bleeding. In addition, upon flowing through the openings 34, 35, the adhesive is prevented from flowing beyond the targeted area of bleeding by the inflated balloon 16. Thereafter, the catheter 10 can be used in ordinary fashion to continue draining fluid from the bladder 15 through the drainage port 22. In addition, the value of a biologic adhesive catheter constructed in accordance with the invention would also apply to patients with urethral stricture disease or scarring of the urethral channel. These patients are treated with either an open repair and reconnection of the urethra or a DVIU which is an incision through the stricture which would then be allowed to heal in an open fashion. These repairs lead to defects in the lining or mucosa of the urinary channel which can lead to urinary extravasation. The ability to deliver a bioadhesive to these areas after repair with the catheter 10 would aid in the healing process and also prevent urinary extravasation. Urinary extravasation is where urine travels beyond the lining of the urinary tract through defects created by repair or incision. The ability to prevent urine extravasation into surrounding tissues may be of value in preventing further scarring. The ability to provide the catheter 10 with tissue glue ports 34, 35 anywhere along the length of the catheter allows one to select a specific catheter depending on the site of injury or repair to aid in the healing process.

Figure 5:
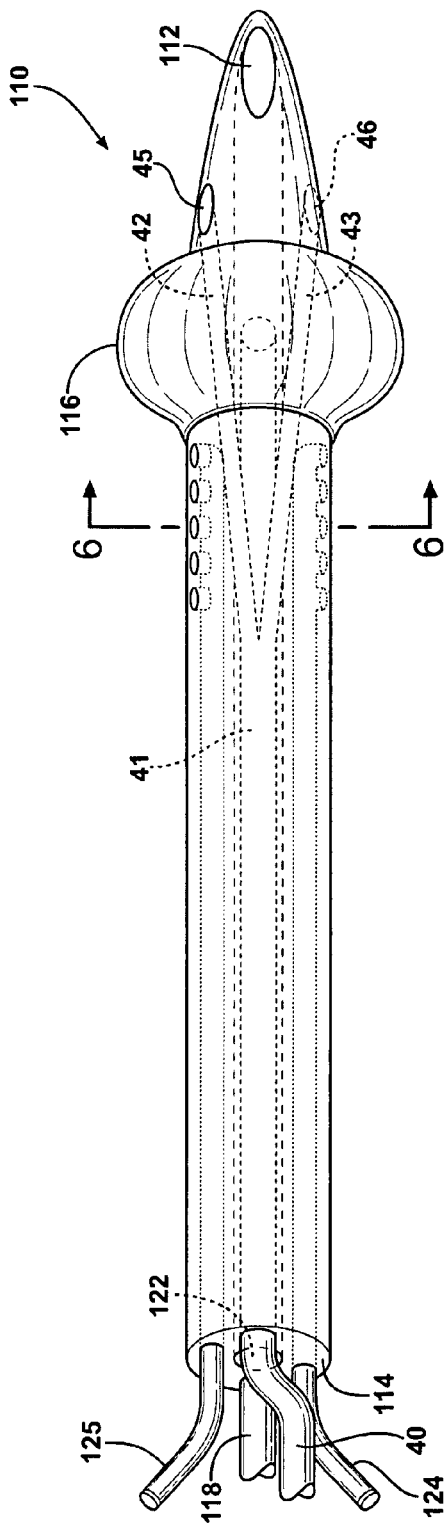
FIG. 5 is a side view of a catheter constructed in accordance with another presently preferred embodiment of the invention having a biologic adhesive system, an irrigation system and a drainage system.
Figure 6:
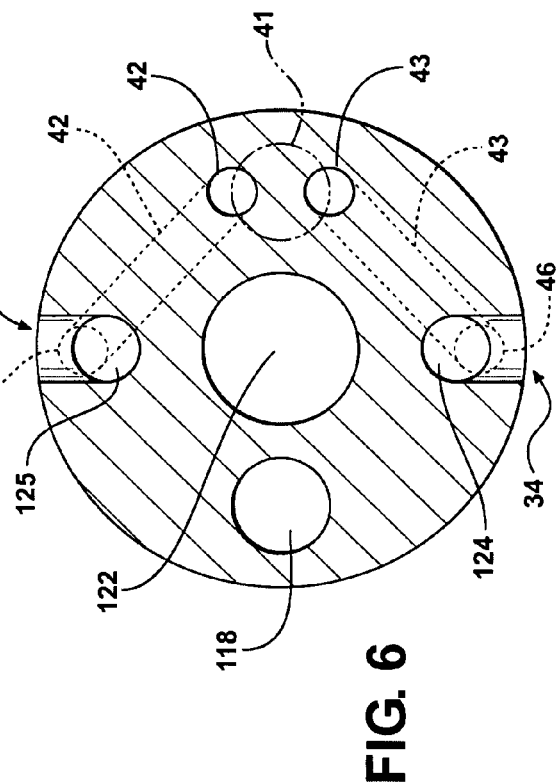
FIG. 6 is a cross-sectional view taken generally along the line 6-6 of FIG. 5.

In FIG. 5, wherein the same reference numerals as used above, offset by a factor of 100, identify similar features as discussed above, a catheter 110 constructed according to another aspect of the invention is illustrated. The catheter 110 is a "three way" catheter in that it provides a fluid drainage system via a fluid drainage port 122, a bioadhesive injection system via a pair of separate bioadhesive ports 124, 125 configured out of fluid communication with one another along the length of their passage through the catheter 110 and extending to respective openings 134, 135, and an irrigation system via another port, also referred to as an irrigation port 40. In addition, the catheter 110 has a balloon 116 that is inflatable via an inflation port 118. The irrigation port 40 is represented as a single port 41 extending generally from the proximal end 114 axially along the catheter, wherein the single port 41 diverges into a pair of ports 42, 43 that open at separate outlets 45, 46 adjacent the distal end 112 between the balloon 116 and the distal end 112. Accordingly, the catheter 110 can be used to inject a two part adhesive, to drain fluid from the bladder, as discussed above, and to irrigate, such as may be beneficial to prevent clot formation.

Obviously, many modifications and variations of the present invention are possible in light of the above teachings. It is, therefore, to be understood that, within the scope of the appended claims and any additional claims ultimately allowed which stem from this or any other related disclosures, the invention may be practiced otherwise than as specifically described.

What is claimed is:
1. A catheter, comprising:
a tubular body extending axially along a longitudinal axis between proximal and distal ends, said tubular body having a balloon adjacent said distal end with a first port, extending between said proximal end and said balloon, in fluid communication with said balloon to provide a mechanism for inflation and deflation of said balloon, said tubular body having a second port extending between said proximal and distal ends across opposite sides of said balloon, said second port remaining out of fluid communication with said first port; and a pair of ports separate from said first and second ports and out of communication with said first and second ports, each of said pair of ports remaining separate from one another and out of fluid communication with one another within said tubular body, each port of said pair of ports has a plurality of openings exiting outwardly from said tubular body between said proximal end and said balloon to provide separate fluid flow paths through said tubular body for separate components of a two part biologic adhesive, said plurality of openings of each port of said pair of ports being substantially radially aligned with one another along a radial plane extending transversely to said longitudinal axis.

2. The catheter of claim 1, wherein each of said plurality of openings are aligned along the longitudinal axis of said tubular body.

3. The catheter of claim 1 wherein said openings are on diametrically opposite sides of said tubular body.

4. The catheter of claim 1 further comprising another port extending between said proximal and distal ends across opposite sides of said balloon.

5. The catheter of claim 4 wherein said another port extends as a single port adjacent said proximal end and diverges into a pair of ports that open at separate outlets adjacent said distal end between said balloon and said distal end.

* * * * *